(12) United States Patent
Randall et al.

(10) Patent No.: US 11,213,524 B2
(45) Date of Patent: Jan. 4, 2022

(54) PHARMACEUTICAL COMPOSITIONS FOR SUBCUTANEOUS ADMINISTRATION OF LEVOSIMENDAN

(71) Applicant: Tenax Therapeutics, Inc., Morrisville, NC (US)

(72) Inventors: Doug Randall, Wake Forest, NC (US); Douglas Hay, Ottsville, PA (US); Nancy J. M. Hecox, Durham, NC (US)

(73) Assignee: TENAX THERAPEUTICS, INC., Morrisville, NC (US)

( * ) Notice: Subject to any disclaimer, the term of this patent is extended or adjusted under 35 U.S.C. 154(b) by 87 days.

(21) Appl. No.: 16/544,098

(22) Filed: Aug. 19, 2019

(65) Prior Publication Data

US 2020/0330463 A1 Oct. 22, 2020

Related U.S. Application Data

(60) Provisional application No. 62/720,260, filed on Aug. 21, 2018.

(51) Int. Cl.
| | | |
|---|---|---|
| *A61K 31/50* | (2006.01) | |
| *A61K 47/40* | (2006.01) | |
| *A61K 9/00* | (2006.01) | |
| *A61K 9/19* | (2006.01) | |

(52) U.S. Cl.
CPC ............... *A61K 31/50* (2013.01); *A61K 47/40* (2013.01); *A61K 9/0019* (2013.01); *A61K 9/19* (2013.01)

(58) Field of Classification Search
CPC ......... A61K 31/50; C07D 237/04; A61P 9/04; A61P 9/12

USPC .......................................... 514/247; 544/224
See application file for complete search history.

(56) References Cited

FOREIGN PATENT DOCUMENTS

| EP | WO2017/077032 | * 11/2017 | ............. A61K 31/50 |
|---|---|---|---|
| WO | WO 2017/077032 | 5/2017 | |

OTHER PUBLICATIONS

International Preliminary Report on Patentability, dated Feb. 23, 2021 by the International Bureau on behalf of the International Searching Authority Under Rule 44 bis.1(a) in connection with the International Application No. PCT/US2019/047032, filed Aug. 19, 2019.

* cited by examiner

*Primary Examiner* — Jeffrey H Murray
(74) *Attorney, Agent, or Firm* — Gary J. Gershik

(57) ABSTRACT

A composition containing levosimendan, one or more solubilizing and/or stabilizing agents, and one or more additional pharmaceutically acceptable additives. The one or more solubilizing and/or stabilizing agents may be a cyclodextrin or a cyclodextrin derivative. The cyclodextrin derivative may be a derivative of an alpha-cyclodextrin, or beta-cyclodextrin, or a gamma-cyclodextrin. The cyclodextrin derivative may contain a butyl ether spacer group, an alkyl ether space group, or both. The one or more additional pharmaceutically acceptable additives may be a non-citrate buffer. The composition may be used in a method of treating a health condition, such as heart failure, pulmonary hypertension, chronic kidney disease, amyotrophic lateral sclerosis, stroke, in advance of a planned cardiac surgery, or other health conditions for which a minimally invasive or repeated administration of levosimendan may be beneficial. The composition may be administered subcutaneously.

19 Claims, 4 Drawing Sheets

PHARMACEUTICAL COMPOSITIONS FOR SUBCUTANEOUS ADMINISTRATION OF LEVOSIMENDAN

CROSS-REFERENCE TO RELATED APPLICATIONS

This application claims the benefit of U.S. Provisional Application Ser. No. 62/720,260 filed on Aug. 21, 2018, the entirety of which is herein incorporated by reference.

FIELD OF THE INVENTION

The present invention is in the field of compositions and treatments for health conditions that require repeated or chronic dosing of levosimendan, and/or where alternative delivery routes for levosimendan such as intravenous (IV) and oral administration are not practical or preferred. In particular, the present invention generally relates to compositions comprising levosimendan for subcutaneous administration to subjects having such health conditions.

BACKGROUND OF THE INVENTION

Levosimendan is an inotropic agent that has been used as a treatment for heart failure and studied as a preventative measure of low cardiac output syndrome after cardiac surgery. Levosimendan increases cardiac contractility mediated by calcium sensitization of troponin C, as well as induces vasodilation based on the opening of K+ channels in the vasculature and cardioprotection due to the opening of mitochondrial K+ channels in the cardiomyocytes. In contrast to beta-adrenergic-receptor-stimulating agents and phosphodiesterase inhibitors, which are both known treatments for heart failure, levosimendan increases the sensitivity of the heart to calcium, which can elevate the strength of contraction without a rise in intracellular calcium.

The potential benefits of repeated doses of levosimendan, which is currently formulated for IV administration, have been investigated for the treatment of chronic heart failure patients. Studies have shown that it is feasible to treat chronic heart failure patients with repeated IV infusions of levosimendan due in large part to a long-acting metabolite of levosimendan, OR-1896, that has a half-life in the range of 70 to 80 hours. While the results of these studies have been generally positive, the commercial feasibility of such use is limited by the significant safety issues created by having chronic indwelling IV lines and the need for repeated and cumbersome IV infusions. In addition, IV administration of levosimendan is absorbed rapidly, which in some patients can lead to acute hypotensive events.

Yet, no other route of administration for levosimendan has been approved. And while other routes of delivery such as subcutaneous administration may address some of these issues associated with IV administration, no known formulations for subcutaneous delivery have been described or investigated. Existing IV formulations of levosimendan are not suitable for other delivery routes such as subcutaneous administration, due to the formulations' low pH. Also, the existing IV formulations rely on excipients such as povidone, anhydrous citric acid, and anhydrous ethanol, which are inherently painful if administered via subcutaneous injection. Further, due to levosimendan's low intrinsic water solubility, it is difficult to formulate levosimendan in water-based parenteral formulations that are sufficiently concentrated and stable in the presence of a physiologically acceptable pH.

Thus, there is a need in the art to develop a formulation of levosimendan that can be delivered through a less invasive, more convenient, and better tolerated route of administration than IV and that is more ideal for treating health conditions that require repeated dosing, such as heart failure, pulmonary hypertension, chronic kidney disease, amyotrophic lateral sclerosis (ALS), and stroke. In addition, some patients may have difficulty swallowing (e.g., patients with ALS, stroke, etc.), and in instances where oral administration is not possible or practical, a different route of administration may be preferred.

SUMMARY OF THE INVENTION

One aspect of the present invention relates to a pharmaceutical composition comprising levosimendan for treatment in subjects in need thereof. The composition may also comprise one or more solubilizing and/or stabilizing agents, and one or more additional pharmaceutically acceptable additives.

In embodiments of the invention, the one or more solubilizing and/or stabilizing agents may comprise a cyclodextrin or a cyclodextrin derivative. In some embodiments, the composition may comprise a cyclodextrin derivative, such as an alpha-cyclodextrin derivative, a beta-cyclodextrin derivative, or a gamma-cyclodextrin derivative. In certain embodiments, the cyclodextrin derivative may comprise a beta-cyclodextrin derivative. In particular embodiments, the cyclodextrin derivative comprises a butyl ether spacer group, an alkyl ether space group, or a combination thereof.

In some embodiments, the cyclodextrin or the cyclodextrin derivative may be present in the composition in an amount of about 1 mg/ml to about 800 mg/ml. In certain embodiments, the cyclodextrin or the cyclodextrin derivative may be present in the composition in an amount of about 50 mg/ml to about 400 mg/ml, or may be present in an amount of about 100 mg/ml to about 300 mg/ml.

In embodiments of the invention, the one or more pharmaceutically acceptable additives may comprise additives that are acceptable for subcutaneous delivery. In some embodiments, the additives may comprise one or more buffering agents, one or more pH-modifying agents, one or more preservatives, one or more antioxidants, one or more carriers, or a combination thereof.

In some embodiments, the composition may comprise a pH of about 5 to about 9. In certain embodiments, the pH may be about 6 to about 8, or may be about 7 to about 8.

In some embodiments, the levosimendan may be present in the composition in an amount of about 0.1 mg/ml to about 100 mg/ml. In certain embodiments, the levosimendan may be present in the composition an amount of about 0.5 mg/ml to about 50 mg/ml, or may be present in an amount of about 1 mg/ml to about 10 mg/ml.

In some embodiments, the composition comprises a non-citrate buffering agent.

In some embodiments, the composition is aqueous. In certain embodiments, the composition is lyophilized.

In some embodiments, the composition is alcohol-free.

In some embodiments, the composition is preservative-free.

In some embodiments, the composition comprises levosimendan, a cyclodextrin or cyclodextrin derivative, and a non-citrate buffer. In certain embodiments, the cyclodextrin derivative is sulfobutylether beta-cyclodextrin; the non-citrate buffer is a phosphate buffer; the composition comprises a pH of about 6 to about 8; and the composition is alcohol-free. In certain embodiments, the composition is in the form of particles. In certain embodiments, the composition is lyophilized or spray-dried.

Another aspect of the invention relates to a method of treating a subject having a health condition, in which the method comprises subcutaneously administering a pharmaceutical composition according to the present invention. The health condition may be heart failure, pulmonary hypertension, chronic kidney disease, ALS, stroke, or other health conditions for which, for example, chronic or repeated administrations of levosimendan may be beneficial.

In some embodiments, the levosimendan may be administered in an amount of about 0.1 mg/day to about 15 mg/day. In certain embodiments, the levosimendan may be administered in an amount of about 1 mg/day to about 10 mg/day.

In some embodiments, the levosimendan may be administered in an amount of about 0.1 mg/week to about 100 mg/week. In certain embodiments, the levosimendan may be administered in an amount of about 1 mg/week to about 20 mg/week.

In some embodiments, the health condition is heart failure. The heart failure may be heart failure with reduced ejection fraction or heart failure with preserved ejection fraction.

Another aspect of the invention relates to a method of improving tolerance to administration of levosimendan, the method comprising subcutaneously administering a pharmaceutical composition according to the present invention.

Another aspect of the invention relates to a method of reducing side effects associated with the administration of levosimendan, the method comprising subcutaneously administering a pharmaceutical composition according to the present invention.

Yet another aspect of the invention relates to a method of enabling delivery of a levosimendan metabolite while minimizing peak plasma concentrations of levosimendan in a subject in need thereof, the method comprising subcutaneously administering a pharmaceutical composition according to the present invention. In some embodiments, the levosimendan metabolite is OR-1896.

Another aspect of the invention relates to a method of treating a patient in need of levosimendan therapy who is unable or unwilling to receive levosimendan treatment by IV or oral delivery, the method comprising subcutaneously administering a pharmaceutical composition according to the present invention.

A further aspect of the invention relates to a method of preparing a pharmaceutical composition according to the present invention.

BRIEF DESCRIPTION OF THE DRAWINGS

For a better understanding of the present invention, reference is made to the following description of an exemplary embodiment thereof, and the accompanying drawing, wherein.

DETAILED DESCRIPTION OF THE INVENTION

Figure 1:
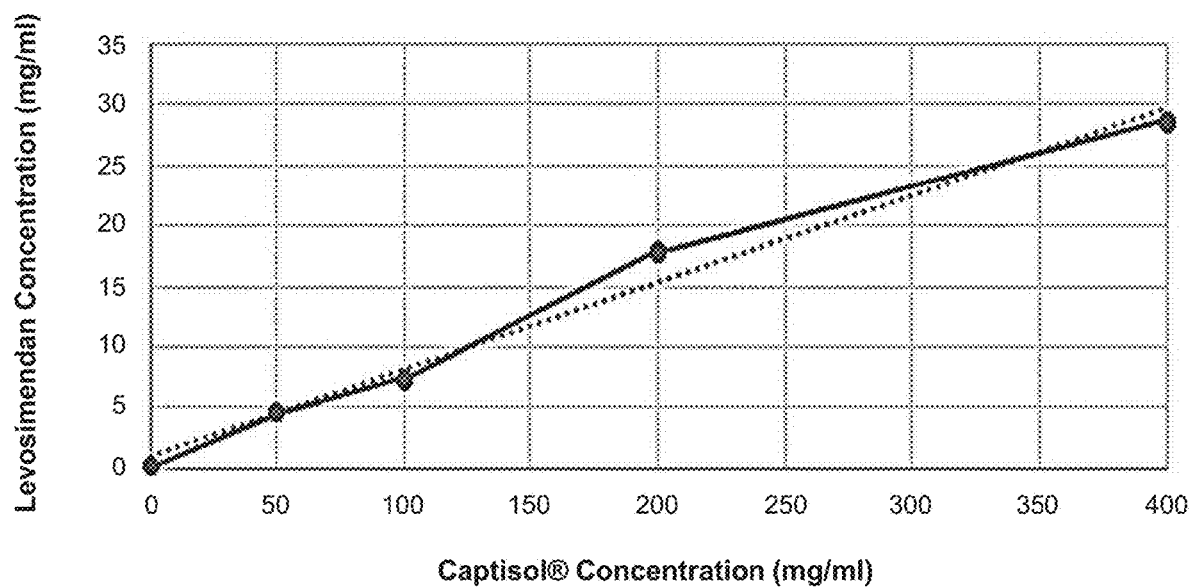
FIG. 1 shows solubility of levosimendan in compositions having different concentrations of Captisol®, as described in Example 1.

The present invention generally relates to pharmaceutical compositions comprising levosimendan for subcutaneous administration. Such pharmaceutical compositions may be used to treat conditions where IV administration is not ideal and/or where a less invasive route of delivery is preferred. The composition may have a more neutral pH, and, optionally, improved solubility and stability as compared to levosimendan compositions known in the art.

The current approved formulations for levosimendan are delivered intravenously, which is not conducive to repeated dosing, such as for treating chronic health conditions. And these formulations are unsuitable for subcutaneous administration, as they have a low pH and comprise, as examples, excipients such as anhydrous ethanol and citrate.

The present invention also relates to subcutaneous administration of levosimendan in pharmaceutical compositions of the present invention for treatment of health conditions, including chronic health conditions. Such administration of levosimendan can be more convenient, especially if treatment requires long-term administration of levosimendan.

Subcutaneous delivery of levosimendan in pharmaceutical compositions of the present invention may be better tolerated than IV delivery. As shown in the Examples presented herein, subcutaneous administration may reduce and delay absorption of levosimendan, resulting in lower plasma concentrations of levosimendan as compared to IV administration. While not being bound by theory, the plasma concentration of levosimendan, in particular the maximum concentration of levosimendan ($C_{max}$), may drive the occurrence of side effects such as hypotensive events, in which higher plasma concentrations and/or higher $C_{max}$ of levosimendan are associated with more side effects or side effects of greater intensity.

Moreover, despite exhibiting a delay in levosimendan absorption and lower levosimendan plasma concentrations, subcutaneous administration of levosimendan in pharmaceutical compositions of the present invention unexpectedly results in a similar plasma concentration profile of the levosimendan metabolite OR-1896 as compared to IV administration. OR-1896 has a long half-life and, as described herein, is considered to be the driver of the sustained efficacy following levosimendan administration. Thus, in other words, subcutaneous administration of levosimendan in pharmaceutical compositions of the present invention provides comparable OR-1896 blood levels as IV administration, but avoids high peak plasma concentrations of levosimendan that can confer a better safety profile. As a result, subcutaneous administration of levosimendan in pharmaceutical compositions of the present invention may be better tolerated and may result in reduced side effects.

In addition, subcutaneous administration of the pharmaceutical composition according to embodiments of the present invention may be less painful than subcutaneous administration of other levosimendan formulations. Formulations that comprise citrate buffers and/or alcohol may cause pain or irritation at the injection site. In contrast, the pharmaceutical composition of the present invention, in some embodiments, may comprise a non-citrate buffer and/or may be free or substantially free of alcohol. Such pharmaceutical compositions can be administered subcutaneously without irritation or any evidence of pain at the injection site, as shown in the Examples presented herein. Thus, the pharmaceutical composition according to embodiments of the present invention can be used to minimize pain during subcutaneous administration of levosimendan.

Levosimendan

Levosimendan (Simdax®) is a calcium sensitizer with vasodilatory and cardioprotective properties. It is potent in the treatment of heart failure and has significant calcium dependent binding to troponin. It is the (−)-enantiomer of [[4-(1,4,5,6-tetrahydro-4-methyl-6-oxo-3-pyridazinyl)phenyl]hydrazono]prop anedinitrile, and methods for its preparation are described in WO 92/12135 and WO 97/35841, which are both incorporated herein by reference in their entireties. Levosimendan has a chemical formula of $C_{14}H_{12}N_6O$, and is represented structurally by formula (I):

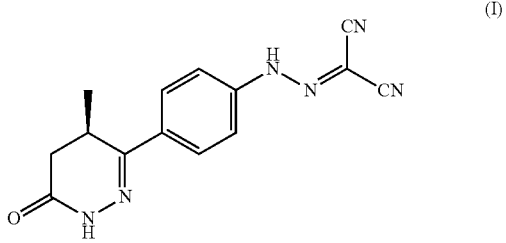 [SMILES: C[C@@H]1CC(=O)NN=C1c1ccc(NN=C(C#N)C#N)cc1]

(I)

Levosimendan is extensively metabolized before excretion into urine and feces. The main pathway is conjugation with glutathione to form inactive metabolites. The minor pathway (approximately 6% of the total levosimendan dose) is reduction in the intestine to an intermediate metabolite OR-1855, represented by formula (II):

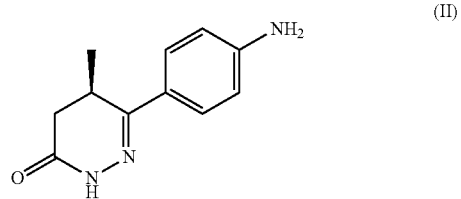

(II)

OR-1855 is further acetylated to an active metabolite, OR-1896. OR-1896 has a chemical formula of $C_{13}H_{15}N_3O_2$, and is represented structurally by formula (III).

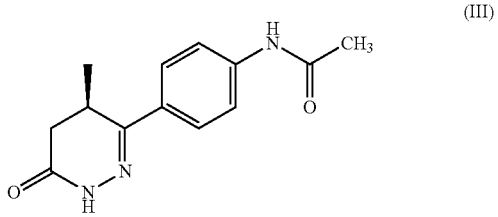 [SMILES: CC(=O)Nc1ccc(C2=NNC(=O)C[C@H]2C)cc1]

(III)

As described previously, OR-1896 is considered to prolong the therapeutic efficacy of levosimendan administration (see, e.g., Kivikko et al., *Int. J. Clin. Pharm. & Ther.*, 2002, 40: 465-71).

In subjects undergoing cardiac surgery, the formation of the metabolites OR-1855 and OR-1896 has been shown to be delayed.

The terminal elimination half-life of levosimendan is about 1 hour. The elimination half-life of the metabolite OR-1896 is 70-80 hours in heart failure patients and the maximum concentrations are only seen 2-4 days after starting a 24-hour infusion.

Levosimendan has a unique pharmacodynamic profile, which differentiates it from other agents typically used in heart failure patients. The drug increases cardiac contractility through calcium sensitization of troponin C. Unlike other positive inotropes, levosimendan is not associated with substantial increases in oxygen demand. It has been demonstrated as a vasodilator of the arterial and venous circulation through its activity on $K_{ATP}$ channels. Further, levosimendan uniquely opens $K_{ATP}$ of mitochondria within cardiomyocytes, an activity associated with reduced apoptosis in nonclinical models and reduced circulating troponin levels in acute decompensated heart failure and cardiac surgery patients.

Levosimendan Compositions

The present invention relates to pharmaceutical compositions that comprise levosimendan. In addition to levosimendan, the compositions may comprise one or more solubilizing and/or stabilizing agents, and one or more other pharmaceutically acceptable additives.

The one or more solubilizing and/or stabilizing agents may comprise agents that enable aqueous solubility. In embodiments of the invention, the one or more solubilizing and/or stabilizing agents may comprise a cyclodextrin or cyclodextrin derivative. Without being bound by theory, the levosimendan and the cyclodextrin or cyclodextrin derivative may form a complex, and this complex may enable levosimendan to become more soluble and stable at physiologic, or near-physiologic, pH. Thus, the resulting composition may have improved aqueous solubility and stability at a pH that is, for example, suitable for subcutaneous injection.

The composition may comprise a cyclodextrin, such an alpha-cyclodextrin, beta-cyclodextrin, and gamma-cyclodextrin, or a combination thereof. In some embodiments, the cyclodextrin may be a beta-cyclodextrin.

The composition may comprise a cyclodextrin derivative of alpha-cyclodextrin, beta-cyclodextrin, or gamma-cyclodextrin. In some embodiments, the cyclodextrin derivative may comprise a spacer group, such as an ether spacer group. Examples of ether spacer groups include, but are not limited to, butyl ether spacer groups, such as sulfobutyl ether groups, and sulfoalkyl ether groups. The number of ether groups attached to the cyclodextrin moiety may vary. For instance, there may be six or seven ether groups per cyclodextrin molecule. Examples of ether groups that may be used with the present invention are described in U.S. Pat. Nos. 7,635,773, 8,049,003, and 9,493,582, which are all incorporated herein by reference in their entireties.

In some embodiments, the cyclodextrin derivative may also comprise a sodium sulfonate salt. The salt may be separated from the lipophilic cavity by the spacer group.

In certain embodiments, the cyclodextrin derivative may comprise a beta-cyclodextrin derivative with a sodium sulfonate salt separated from the lipophilic cavity by a sulfobutylether.

In other embodiments, the cyclodextrin derivative may comprise a sulfobutylether-beta-cyclodextrin such as Captisol®, which is a cyclodextrin technology developed by Ligand Pharmaceuticals.

In embodiments of the invention, the cyclodextrin or the cyclodextrin derivative may be present in an amount of about 1 mg/ml to about 800 mg/ml. In some embodiments, the cyclodextrin or the cyclodextrin derivative may be present in an amount of about 50 mg/ml to about 400 mg/ml, or may be present in an amount of about 100 mg/ml to about 300 mg/ml. In certain embodiments, the cyclodextrin or the cyclodextrin derivative may be present in an amount of about 200 mg/ml.

In certain embodiments, the composition may comprise a sulfobutylether-beta-cyclodextrin such as Captisol® in an amount of about 200 mg/ml.

The pharmaceutical composition may comprise one or more pharmaceutically acceptable additives, such as additives that are acceptable for subcutaneous delivery. In embodiments of the invention, the one or more pharmaceutically acceptable additives may be one or more buffering agents, one or more pH-adjusting agents, one or more tonicity-adjusting agents, one or more preservatives, one or more antioxidants, one or more carriers, or a combination thereof.

In some embodiments, the composition may comprise one or more non-citrate buffering agents. Such non-citrate buffering agents for use in the composition may include, but are not limited to, 1,3-bis(tris(hydroxymethyl)methylamino)propane ("bis-tris propane"), 2-(carbamoylmethylamino)ethanesulfonic acid ("ACES"), 2-(N-morpholino)ethanesulfonic acid ("MES"), 2-[(2-amino-2-oxoethyl)-(carboxymethyl)amino]acetic acid ("ADA"), 2-[Bis(2-hydroxyethyl)amino]-2-(hydroxymethyl)propane-1,3-diol ("bis-tris methane"), 3-morpholino-2-hydroxypropanesulfonic acid ("MOPSO"), acetate, alpha-lipoic acid, ascorbate, benzoate, bicarbonate, cacodylate, carbonate, chloroacetate, formate, gentisate, glycine, histidine, imidazole, lactate, lactobionate, malate, maleate, phosphate, piperazine-N,N'-bis(2-ethanesulfonic acid) ("PIPES"), propionate, pyridine, pyrophosphate, succinate, tartrate, tris(hydroxymethyl)aminomethane ("TRIS"), or a combination thereof. In certain embodiments, the composition comprises phosphate as a buffering agent, such as a 10 mM phosphate buffer.

In some embodiments, the composition may comprise one or more pH-adjusting agents. A pH-adjusting agent is a pharmaceutically acceptable component or reagent that is used to adjust the final pH of the composition, the pH during the preparation of the composition, and/or the pH of one or more buffering agents. The pH-adjusting agent may include pharmaceutically acceptable acids or bases. For example, the acids may include, but are not limited to, one or more inorganic mineral acids such as hydrochloric, hydrobromic, sulfuric, phosphoric, nitric, and the like; one or more organic acids such as acetic, succinic, tartaric, ascorbic, citric, glutamic, benzoic, methanesulphonic, ethanesulfonic, trifluoroacetic, and the like; or combinations thereof. The bases may be one or more inorganic bases or organic bases, including, but not limited to, alkaline carbonate, alkaline bicarbonate, alkaline earth metal carbonate, alkaline hydroxide, alkaline earth metal hydroxide, or amine, or combinations thereof. For example, the inorganic or organic base may be an alkaline hydroxide such as lithium hydroxide, potassium hydroxide, cesium hydroxide, sodium hydroxide or the like; an alkaline carbonate such as calcium carbonate, sodium carbonate or the like; an alkaline bicarbonate such as sodium bicarbonate or the like; or combinations thereof. In some embodiments, the organic base may be sodium acetate.

In some embodiments, the composition of the present invention comprises a pH of about 5 to about 9, or about 6 to about 8, or about 7 to about 8. In certain embodiments, the composition comprises a pH of about 7.4. In certain embodiments, the composition comprises a neutral pH. In certain embodiments, the pH of the composition is at or near physiological pH.

In some embodiments, the composition may comprise one or more tonicity-adjusting agents. Tonicity-adjusting agents are agents that adjust the composition to the desired isotonic range. The tonicity agents that may be used in the compositions may include, but are not limited to, pharmaceutically acceptable inorganic chlorides such as sodium chloride, potassium chloride, magnesium chloride, or calcium chloride; sugars such as dextrose, glycerol, lactose, sucrose, mannitol, sorbitol, and the like; or combinations thereof.

In some embodiments, the composition may comprise an osmolality of about 100 mOsm/kg to about 3000 mOsm/kg, or about 200 mOsm/kg to about 1000 mOsm/kg.

In some embodiments, the composition may comprise one or more preservatives. Preservatives may include, but are not limited to, benzalkonium chloride, bronopol, cetrimide ("cetyltrimethylammonium bromide"), benzoic acid, benzyl alcohol, borates, chlorhexidine, chlorobutanol, nitrates, alkyl parabens including methyl- and ethyl- and propyl-paraben, phenylmercuric acetate, potassium sorbate, sodium benzoate, sorbic acid, thiomersal ("mercurithiosalicylate"), or combinations thereof.

In some embodiments, the composition does not comprise a preservative, i.e., the composition is preservative-free.

Further, in some embodiments, the composition may comprise one or more antioxidants. Antioxidants may be selected from, but are not limited to, acetylcysteine, ascorbyl palmitate, butylated hydroxyanisole ("BHA"), butylated hydroxytoluene ("BHT"), monothioglycerol, potassium nitrate, sodium ascorbate, sodium formaldehyde sulfoxylate, sodium metabisulfite, sodium bisulfite, vitamin E or a derivative thereof, propyl gallate, edetate ("EDTA") (e.g., disodium edetate), diethylenetriaminepentaacetic acid ("DTPA"), triglycollamate ("NT"), or a combination thereof. Antioxidants may also comprise amino acids such as methionine, histidine, cysteine, and those carrying a charged side chain, such as arginine, lysine, aspartic acid, and glutamic acid. Any stereoisomer (e.g., L-, D-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form. For example, the L-stereoisomer may be used.

In some embodiments, the composition may comprise one or more carriers. Examples of carriers include liquid media such as solutions, suspensions, hydrogels, liposomes, and emulsions. Such carriers may in part alter the absorption characteristics in a way that extend the effectiveness and or minimize side effects.

Levosimendan may be dissolved or suspended in a pharmaceutically acceptable liquid carrier that may comprise an organic solvent, and/or pharmaceutically acceptable oils and/or fats.

In some embodiments, the pharmaceutical composition of the present invention may include other suitable pharmaceutical additives such as solubilizers, emulsifiers, sweeteners, flavoring agents, suspending agents, thickening agents, colors, viscosity regulators, stabilizers, and/or osmo-regulators.

In some embodiments, the composition is substantially free of alcohol. In this context, "substantially free of alcohol" means that the composition contains less than about 5%, or less than about 4%, or less than about 3%, or less than about 2%, or less than about 1%, or less than about 0.5%, or less than about 0.1%, alcohol. In certain embodiments, the composition is alcohol-free, meaning that there is no measurable amount of alcohol in the composition.

In some embodiments, the composition comprises levosimedan, a cyclodextrin or cyclodextrin derivative, and a non-citrate buffer. In certain embodiments, the cyclodextrin derivative is sulfobutylether beta-cyclodextrin; the non-citrate buffer is a phosphate buffer; the composition comprises a pH of about 6 to about 8; and the composition is alcohol-free.

In some embodiments, the composition may be water-soluble.

In some embodiments, the composition may be in an aqueous form. In certain embodiments, the composition may be ready-to-use, in which the composition has not been reconstituted from a lyophilizate within one day prior to use.

In other embodiments, the composition may be in the form of particles. In certain embodiments, the composition may be lyophilized, such as the result of lyophilizing the aqueous form; or may be spray-dried, such as the result of spray-drying the aqueous form. Prior to use, the lyophilized may be reconstituted with an aqueous solution for injection, such as water for injection or saline.

The pharmaceutical composition of the present invention may achieve a level of solubility of levosimendan that is suitable for subcutaneous administration. For instance, the amount of levosimendan in a pharmaceutical composition can be about 0.1 mg/ml or greater, or about 0.5 mg/ml or greater, or about 1 mg/ml or greater, or about 2 mg/ml or greater, or about 3 mg/ml or greater, or about 4 mg/ml or greater, or about 5 mg/ml or greater, about 8 mg/ml or greater, or about 10 mg/ml or greater. In various embodiments, the amount of levosimendan can be about 15 mg/ml or greater, or about 20 mg/ml or greater, or about 25 mg/ml or greater, or about 30 mg/ml or greater, or about 40 mg/ml or greater, or about 50 mg/ml or greater. In some embodiments, levosimendan may be present in an amount of about 0.1 mg/ml to about 100 mg/ml, or about 1 mg/ml to about 30 mg/ml, or about 1 mg/ml to about 25 mg/ml, or about 1 mg/ml to about 20 mg/ml, or about 2 mg/ml to about 15 mg/ml, or about 2 mg/ml to about 10 mg/ml. In some embodiments, levosimendan may be present in an amount of about 2 mg/ml, or about 3 mg/ml, or about 4 mg/ml, or about 5 mg/ml, about 6 mg/ml, or about 8 mg/ml, or about 10 mg/ml, or about 12 mg/ml, or about 15 mg/ml, or about 20 mg/ml, or about 30 mg/ml, or about 40 mg/ml, or about 50 mg/ml, or any amount therebetween. In certain embodiments, levosimendan may be present in an amount of about 0.1 mg/ml to about 10 mg/ml, or about 0.5 mg/ml to about 5 mg/ml.

In certain embodiments, the composition may comprise 3 mg/ml of levosimendan, 200 mg/ml of sulfobutylether beta-cyclodextrin, and 10 mM of phosphate buffer.

In some embodiments, the composition of the present invention is stable. The stability of the composition may be demonstrated by different measures. For instance, the composition may exhibit a particular purity, either w/w or % as measured by high performance liquid chromatography (HPLC), under certain storage conditions over a specified period of time. The purity may be at least 99%, or at least 98%, or at least 95%, or at least 90%, or at least 85%, or at least 80%, or at least 75%, or at least 70%. In some embodiments, the quantity of OR-1420, a known degradant of levosimendan represented by formula (IV), is less than about 2%, or less than about 1%, or less than about 0.5%, as measured by HPLC. In certain embodiments, the quantity of OR-1420 is less than 1%, or less than 0.9%, or less than 0.8%, or less than 0.7%, or less than 0.6%, or less than 0.5%, as measured by HPLC.

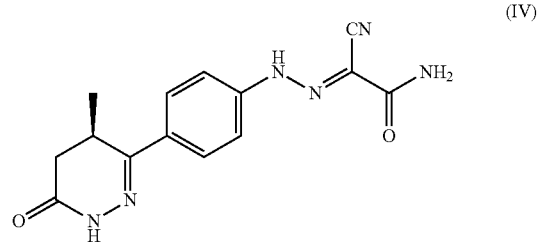 [SMILES: C[C@@H]1CC(=O)NN=C1c1ccc(N/N=C(\C#N)C(N)=O)cc1]

(IV)

The storage conditions may be one or more of about 25° C./60% RH, or about 30° C./65% RH, or about 40° C./75% RH. The period of time may be one or more of about 1 week, or about 2 weeks, or about 1 month, or about 2 months, or about 3 months, or about 4 months, or about 6 months, or about 9 months, or about 12 months, or about 15 months, or about 18 months, or about 21 months, or about 2 years, or any period of time therebetween.

Methods of Treatment

An aspect of the present invention relates to the use of levosimendan by subcutaneous administration to subjects in need thereof.

Embodiments of the present invention relate to (i) methods of treating a health condition; (ii) methods of improving tolerance to administration of levosimendan; (iii) methods of reducing side effects associated with the administration of levosimendan; (iv) methods of enabling delivery of a levosimendan metabolite while minimizing peak plasma concentrations of levosimendan; (v) methods of treating a patient in need of levosimendan therapy who is unable or unwilling to receive levosimendan treatment by IV or oral delivery; and (vi) methods of minimizing pain during subcutaneous administration of levosimendan. These methods may comprise subcutaneously administering a pharmaceutical composition according to the present invention to the subject in need thereof.

Embodiments of the present invention relate to uses of levosimendan for (i) treating a health condition; (ii) improving tolerance to administration of levosimendan; (iii) reducing side effects associated with the administration of levosimendan; (iv) enabling delivery of a levosimendan metabolite while minimizing peak plasma concentrations of levosimendan; (v) treating a patient in need of levosimendan therapy who is unable or unwilling to receive levosimendan treatment by IV or oral delivery; and (vi) minimizing pain during subcutaneous administration of levosimendan. These uses may comprise subcutaneously administering a pharmaceutical composition according to the present invention to the subject in need thereof.

Embodiments of the present invention relate to uses of levosimendan in the manufacture of a medicament for (i) treating a health condition; (ii) improving tolerance to administration of levosimendan; (iii) reducing side effects associated with the administration of levosimendan; (iv) enabling delivery of a levosimendan metabolite while minimizing peak plasma concentrations of levosimendan; (v) treating a patient in need of levosimendan therapy who is unable or unwilling to receive levosimendan treatment by IV or oral delivery; and (vi) minimizing pain during subcutaneous administration of levosimendan. This treatment of a health condition, improvement in the tolerance to administration of levosimendan, reduction in side effects associated with the administration of levosimendan, enablement of delivery of a levosimendan metabolite while minimizing peak plasma concentrations of levosimendan, treatment of a patient in need of levosimendan therapy who is unable or unwilling to receive levosimendan treatment by IV or oral delivery, and minimization of pain during subcutaneous administration of levosimendan, may comprise subcutaneously administering a pharmaceutical composition according to the present invention to the subject in need thereof.

Additional embodiments of the present invention relate to levosimendan for use in (i) treating a health condition; (ii) improving tolerance to administration of levosimendan; (iii) reducing side effects associated with the administration of levosimendan; (iv) enabling delivery of a levosimendan metabolite while minimizing peak plasma concentrations of levosimendan; (v) treating a patient in need of levosimendan therapy who is unable or unwilling to receive levosimendan treatment by IV or oral delivery; and (vi) minimizing pain during subcutaneous administration of levosimendan. This treatment of a health condition, improvement in the tolerance to administration of levosimendan, reduction in side effects associated with the administration of levosimendan, enablement of delivery of a levosimendan metabolite while minimizing peak plasma concentrations of levosimendan, treatment of a patient in need of levosimendan therapy who is unable or unwilling to receive levosimendan treatment by IV or oral delivery, and minimization of pain during subcutaneous administration of levosimendan, may comprise subcutaneously administering a pharmaceutical composition according to the present invention to the subject in need thereof.

Further embodiments of the present invention relate to a pharmaceutical composition of the present invention for use in (i) treating a health condition; (ii) improving tolerance to administration of levosimendan; (iii) reducing side effects associated with the administration of levosimendan; (iv) enabling delivery of a levosimendan metabolite while minimizing peak plasma concentrations of levosimendan; (v) treating a patient in need of levosimendan therapy who is unable or unwilling to receive levosimendan treatment by IV or oral delivery; and (vi) minimizing pain during subcutaneous administration of levosimendan. This treatment of a health condition, improvement in the tolerance to administration of levosimendan, reduction in side effects associated with the administration of levosimendan, enablement of delivery of a levosimendan metabolite while minimizing peak plasma concentrations of levosimendan, treatment of a patient in need of levosimendan therapy who is unable or unwilling to receive levosimendan treatment by IV or oral delivery, and minimization of pain during subcutaneous administration of levosimendan, may comprise subcutaneously administering the pharmaceutical composition according to the present invention to the subject in need thereof.

The metabolite delivered to the subject may be OR-1896 or OR-1855. In some embodiments, the metabolite is OR-1896.

The pharmaceutical composition may be administered in an amount that will provide about 0.1 mg/day to about 15 mg/day, or about 0.5 mg/day to about 10 mg/day, of levosimendan. In some embodiments, the pharmaceutical composition may be administered in an amount that will provide about 0.5 mg/day to about 10 mg/day of levosimendan.

The pharmaceutical composition may be administered in an amount that will provide about 0.5 mg/week to about 100 mg/week of levosimendan. In some embodiments, the pharmaceutical composition may be administered in an amount that will provide about 1 mg/week to about 20 mg/week of levosimendan.

The pharmaceutical composition may be administered as divided doses. For example, the pharmaceutical composition may be administered once per day, or twice per day, or three times a day, or four times per day, or five times per day. Other examples of divided doses include, but are not limited to, once per week, twice per week, three times per week, four times per week, or five times per week.

In some embodiments, pharmaceutical composition may be administered continuously or intermittently via a subcutaneous delivery device, for example, a subcutaneous pump, micropump, or patch device.

In some embodiments, the pharmaceutical compositions of the present invention may be capable of administration by parenteral routes besides subcutaneous, such as IV or intramuscularly.

In some embodiments, the pharmaceutical composition may be in powder form such as lyophilized or spray-dried. Thus, the method comprises reconstituting the composition in an aqueous solution for injection, and then administering the reconstituted composition to the subject. The aqueous solution may comprise those known in the art, such as water for injection or saline.

Subcutaneous administration of a pharmaceutical composition of the present invention can minimize peak levosimendan plasma concentrations.

Subcutaneous administration of a pharmaceutical composition of the present invention may result in a pharmacokinetic profile for levosimendan that is different than the pharmacokinetic profile for levosimendan that results from IV administration of the same dose of levosimendan, such as IV administration of a standard commercial, IV formulation of levosimendan (e.g., Simdax®). For example, in some embodiments, after a single subcutaneous administration to a subject of a pharmaceutical composition of the present invention, the bioavailability of levosimendan may be no more than about 75%, or no more than about 70%, or no more than about 65%, or no more than about 60%, or no more than about 55%, or no more than about 50%, or no more than about 45%, or no more than about 40%, or no more than about 35%, or no more than about 30%, of the bioavailability of levosimendan after a single IV administration of the same dose of levosimendan. In some embodiments, the bioavailability of levosimendan after a single subcutaneous administration to a subject of a pharmaceutical composition of the present invention may be about 5% to about 75%, or about 5% to about 70%, or about 5% to about 65%, or about 10% to about 60%, or about 10% to about 55%, or about 10% to about 50%, or about 15% to about 45%, or about 20% to about 40%, or about 20% to about 35%, of the bioavailability of levosimendan after a single IV administration of the same dose of levosimendan. Bioavailability may be measured by area-under-the-curve (AUC), such as $AUC_{(0-last)}$ and/or $AUC_{(0-inf)}$.

In some embodiments, after a single subcutaneous administration to a subject of a pharmaceutical composition of the present invention, the maximum concentration ($C_{max}$) of levosimendan may be no more than about 75%, or no more than about 70%, or no more than about 65%, or no more than about 60%, or no more than about 55%, or no more than about 50%, or no more than about 45%, or no more than about 40%, or no more than about 35%, or no more than about 30%, or no more than about 25%, or no more than about 20%, or no more than about 15%, of the $C_{max}$ of levosimendan after a single IV administration of the same dose of levosimendan. In some embodiments, the $C_{max}$ of levosimendan after a single subcutaneous administration to a subject of a pharmaceutical composition of the present invention may be about 1% to about 70%, or about 1% to about 65%, or about 1% to about 60%, or about 1% to about 55%, or about 1% to about 50%, or about 5% to about 45%, or about 5% to about 40%, about 5% to about 35%, or about 5% to about 30%, or about 5% to about 25%, or about 5% to about 20%, or about 10% to about 15%, of the $C_{max}$ of levosimendan after a single IV administration of the same dose of levosimendan.

In some embodiments, after a single subcutaneous administration to a subject of a pharmaceutical composition of the present invention, the time to maximum concentration ($T_{max}$) of levosimendan may be within about 4 hours, or within about 3.5 hours, or within about 3 hours, or within about 2.5 hours, or within about 2 hours, or within about 1.5 hours, or within about 1 hour, or within about 30 minutes, of the $T_{max}$ of levosimendan after a single IV administration of the same dose of levosimendan. In some embodiments, the $T_{max}$ for levosimendan after a single subcutaneous administration to a subject of a pharmaceutical composition of the present invention may be less than about 2 hours, or less than about 1.5 hours, or less than about 1 hour, from the $T_{max}$ of levosimendan after a single IV administration of the same dose of levosimendan.

Subcutaneous administration of a pharmaceutical composition of the present invention may result in a pharmacokinetic profile for a levosimendan metabolite, OR-1896, that is similar to the pharmacokinetic profile for OR-1896 that results from IV administration of the same dose of levosimendan, such as IV administration of a standard commercial, IV formulation of levosimendan (e.g., Simdax®). For example, after a single subcutaneous administration to a subject of a pharmaceutical composition of the present invention, the bioavailability of OR-1896 may be at least about 70%, or at least about 75%, or at least about 80%, or at least about 85%, or at least about 90%, of the bioavailability of OR-1896 after a single IV administration of the same dose of levosimendan. In some embodiments, the bioavailability of OR-1896 after a single subcutaneous administration to a subject of a pharmaceutical composition of the present invention may be about 70% to about 110%, or about 75% to about 105%, or about 80% to about 100%, of the bioavailability of OR-1896 after a single IV administration of the same dose of levosimendan. Bioavailability may be measured by area-under-the-curve (AUC), such as $AUC_{(0-last)}$ and/or $AUC_{(0-inf)}$.

In some embodiments, after a single subcutaneous administration to a subject of a pharmaceutical composition of the present invention, the $C_{max}$ of OR-1896 may be at least about 80%, or at least about 85%, or at least about 90%, or at least about 95%, or at least about 100%, or at least about 105%, or at least about 110%, or at least about 115%, or at least about 120%, of the $C_{max}$ of OR-1896 after a single IV administration of the same dose of levosimendan. In some embodiments, the $C_{max}$ of OR-1896 after a single subcutaneous administration to a subject of a pharmaceutical composition of the present invention may be about 80% to about 120%, or about 85% to about 115%, or about 90% to about 110%, of the $C_{max}$ of OR-1896 after a single IV administration of the same dose of levosimendan.

In some embodiments, after a single subcutaneous administration to a subject of a pharmaceutical composition of the present invention, the $T_{max}$ of OR-1896 may be within about 4 hours, or within about 3.5 hours, or within about 3 hours, or within about 2.5 hours, or within about 2 hours, or within about 1.5 hours, or within about 1 hour, or within about 30 minutes, of the $T_{max}$ of OR-1896 after a single IV administration of the same dose of levosimendan. In some embodiments, the $T_{max}$ for OR-1896 after a single subcutaneous administration to a subject of a pharmaceutical composition of the present invention may be less than about 2 hours, or less than about 1.5 hours, or less than about 1 hour, from the $T_{max}$ of OR-1896 after a single IV administration of the same dose of levosimendan.

The health condition according to the present invention may be a medical condition in which administration of levosimendan via a non-IV route of delivery, such as subcutaneous, is preferred. In some embodiments, the health condition is a medical condition that requires repeated dosing. Examples of health conditions may include, but are not limited to, heart failure, pulmonary hypertension, essential hypertension, secondary hypertension, chronic kidney disease, renal failure, nephropathy, chronic obstructive pulmonary disease, Raynaud's disease, peripheral vascular disease, cardio-renal syndrome, Alzheimer's, ALS, neurodegenerative disease, stroke, cerebrovascular disease, muscular dystrophy, congenital heart disease, cardiomyopathy, and other health conditions for which the repeated dosing of levosimendan may be beneficial, such as other diseases that may benefit from levosimendan's calcium sensitizing and K-ATP channel activation mechanisms, or in advance of a planned cardiac surgery.

In some embodiments, the health condition comprises heart failure. The heart failure may be either heart failure with reduced ejection fraction (HFrEF) or heart failure with preserved ejection fraction (HFpEF).

In some embodiments, the health condition comprises pulmonary hypertension. The pulmonary hypertension may be pulmonary hypertension due to heart failure with reduced ejection fraction (PH-HFrEF) or pulmonary hypertension due to heart failure with preserved ejection fraction (PH-HFpEF). The pulmonary hypertension may also be pulmonary arterial hypertension (PAH) or other World Health Organization (WHO) Group 1-5 classifications or pulmonary hypertension.

The subject as used herein may be a mammal, such as a human.

Methods of Preparing the Composition

The present invention also relates to a method of preparing a composition of the invention. The method comprises admixing levosimendan with the one or more solubilizing and/or stabilizing agents, and the one or more pharmaceutically acceptable additives.

In some embodiments, the method further comprises placing the resulting admixture into powder form, such as by lyophilizing or spray drying the admixture.

This invention will be better understood by reference to the Example that follows, but those skilled in the art will readily appreciate that the specific experiment detailed is only illustrative of the invention as described more fully in the claims which follow thereafter.

EXAMPLES

Example 1

A study was conducted to evaluate the impact of the concentration of the cyclodextrin or cyclodextrin derivative on the solubility of levosimendan. In particular, the study focused on the cyclodextrin derivative, Captisol® (sulfobutylether beta-cyclodextrin).

The study compared compositions comprising levosimendan, 10 mM phosphate buffer, and Captisol® at the following concentrations: 0 mg/ml (i.e., no Captisol®), 50 mg/ml, 100 mg/ml, 200 mg/ml, and 400 mg/ml. The compositions with Captisol® were prepared by mixing the levosimendan and Captisol®, and adding the 10 mM phosphate buffer until the pH of the composition was 7. The compositions were stored at room temperature.

Captisol®'s impact on the solubility of levosimendan was determined using HPLC. The results showed that the solubility of levosimendan increased as the concentration of Captisol® increased. As shown in FIG. 1, the solubility of levosimendan and the Captisol® concentration shared a near-linear relationship.

Example 2

A study was conducted to determine the stability of a levosimendan composition of the present invention stored under different conditions for up to six months.

The composition used for the study comprised 3 mg/ml of levosimendan and 200 mg/ml of Captisol®. To prepare the composition, the levosimendan and Captisol® were mixed together, adjusted to a pH of 7.4 using 1N NaOH, and then lyophilized.

A single sample of the composition was stored under each of the conditions shown in Table 1 below.

TABLE 1

Conditions under which the compositions were stored.

| Condition No. | Storage Conditions |
|---|---|
| 1 | −80° C. |
| 2 | −20° C. |
| 3 | 5° C. |
| 4 | 25° C./60% RH |
| 5 | 40° C./75% RH |

Samples were dissolved in 50% acetonitrile and stored frozen at approximately −20° C. The compositions were analyzed at the following time points: 0, 1-month, 2-months, 4-months, and 6-months. The compositions were taken out of storage and reconstituted using distilled water. A sample from each composition was diluted at 15x-150x and analyzed using HPLC (Sciex API 3200 Linear Ion Trap, Shimadzu LC-20ADVP HPLC Pumps, Shimadzu Controller SCL-10AVP, Shimadzu Autosampler SIL-20ADVP) under the following conditions: Column, Restek Raptor Biphenyl, 2.7 μm, 100×3 mm; Mobile phase A, 5 mM Ammonium Formate/0.1% FA in H$_2$O; Mobile phase B, 100% methanol).

The analysis of the samples determined how the storage conditions impacted the quantity of levosimendan in the composition over time. The results, presented in Table 2, shows that the levosimendan in the composition was stable, as for each storage condition the level of levosimendan remained at over 98% after six months.

TABLE 2

Stability of levosimendan under different storage conditions.

| Storage Conditions | Levels of Levosimendan (% Area) | | | | |
|---|---|---|---|---|---|
| | T$_0$ | 1-month | 2-months | 4-months | 6-months |
| T$_0$ | 99.98% | n/a | n/a | n/a | n/a |
| −80° C. | n/a | 99.82% | NA | 99.74% | 99.74% |
| −20° C. | n/a | 99.83% | NA | 99.79% | 99.72% |
| 5° C. | n/a | 99.85% | 100.00% | 99.74% | 99.73% |
| 25° C./60% RH | n/a | 99.75% | 99.79% | 99.51% | 99.49% |
| 40° C./75% RH | n/a | 99.51% | NA | 98.88% | 98.37% | n/a = not applicable;
NA = not analyzed

The analysis also assessed for the presence of degradants in the samples. Tables 3 and 4 shows the HPLC measurements of degradants under different storage conditions after four months and six months, respectively.

TABLE 3

Presence of degradants under different storage conditions after four months.

| Degradant | Retention Time (min) | RRT | Level of Degradants (% Area) | | | | |
|---|---|---|---|---|---|---|---|
| | | | −80° C. | −20° C. | 5° C. | 25° C./60% RH | 40° C./75% RH |
| Peak1 | 1.3 | 0.102 | 0.020 | 0.020 | 0.020 | 0.037 | 0.074 |
| OR-1420 | 8.2 | 0.641 | 0.084 | 0.045 | 0.057 | 0.285 | 0.999 |
| Peak 10 m | 10.5 | 0.820 | 0.01 | 0.005 | 0.007 | 0.034 | 0.070 |
| Levosimendan | 12.8 | 1.000 | 99.89 | 99.93 | 99.91 | 99.64 | 99.81 |
| Other Total Rel | NA | NA | NA | NA | NA | NA | 0.046 |

NA = not analyzed

TABLE 4

Presence of degradants under different storage conditions after six months.

| Degradant | Retention Time (min) | RRT | Level of Degradants (% Area) | | | | |
|---|---|---|---|---|---|---|---|
| | | | −80° C. | −20° C. | 5° C. | 25° C./60% RH | 40° C./75% RH |
| Peak1 | 1.3 | 0.102 | 0.018 | 0.016 | 0.017 | 0.030 | 0.104 |
| OR-1420 | 8.2 | 0.641 | 0.083 | 0.082 | 0.112 | 0.377 | 1.42 |
| Peak 10 m | 10.5 | 0.820 | 0.006 | 0.006 | ND | 0.024 | 0.024 |
| Levosimendan | 12.8 | 1.000 | 99.89 | 99.89 | 99.90 | 99.57 | 98.35 |
| Other Total Rel | NA | NA | NA | NA | NA | NA | 0.106 |

NA = not analyzed

The analysis further investigated the presence of degradant OR-1420 in particular. Table 5 shows how, under the more extreme storage condition of 40° C./75% RH, the quantity of OR-1420 remained below 1.5% after 6 months. For all other storage conditions, the quantity of OR-1420 was less than 0.5% after 6 months.

TABLE 5

Presence of degradant OR-1420 under different storage conditions.

| Storage Conditions | Level of OR-1420 (% Area) | | | | |
|---|---|---|---|---|---|
| | $T_0$ | 1-month | 2-months | 4-months | 6-months |
| $T_0$ | 0.021% | n/a | n/a | n/a | n/a |
| −80° C. | n/a | 0.055% | NA | 0.084% | 0.083% |
| −20° C. | n/a | 0.050% | NA | 0.045% | 0.082% |
| 5° C. | n/a | 0.055% | ND | 0.057% | 0.112% |
| 25° C./60% RH | n/a | 0.155% | 0.212% | 0.285% | 0.377% |
| 40° C./75% RH | n/a | 0.436% | NA | 0.999% | 1.420% | n/a = not applicable;
NA = not analyzed;
ND = not detected

The results of this study showed that a levosimendan composition in accordance with the present invention demonstrated stability for up to six months across different storage conditions, including the accelerated storage condition of 40° C./75% RH. Such stability is ideal for a composition formulated for subcutaneous administration.

Example 3

A pharmacokinetic study was conducted in male Sprague Dawley rats to compare subcutaneous administration of a composition of the present invention with IV administration of a formulation of levosimendan. The study evaluated levosimendan blood levels and pain at the injection site.

Methodology

This study involved comparing the results of administering two subcutaneous compositions according to embodiments of the present invention to a previous pharmacokinetic study in which male rats were dosed by tail vein levosimendan as an IV bolus injection at 0.5 mg/kg using a 0.25 mg/ml solution. Thus, this study comprised three study arms:

(1) IV administration of a composition comprising levosimendan (0.25 mg/ml) and phosphate buffer (10 mmolar), prepared in sterile water for injection and adjusted to a pH of 7.0 to 7.9 using 1 N NaOH or 10 N NaOH; this composition was administered at a dose of 0.5 mg/kg.

(2) Subcutaneous administration of a composition comprising levosimendan (1.0 mg/ml), Captisol® (100 mg/ml), and phosphate buffer (10 mmolar), prepared in sterile water for injection and adjusted to a pH of 7.0 to 7.9 using 1 N NaOH or 10 N NaOH; this composition was administered at a dose of 0.5 mg/kg.

(3) Subcutaneous administration of a composition comprising levosimendan (1.0 mg/ml), Captisol® (300 mg/ml), and phosphate buffer (10 mmolar), prepared in sterile water for injection and adjusted to a pH of 7.0 to 7.9 using 1 N NaOH or 10 N NaOH; this composition was administered at a dose of 0.5 mg/kg.

Each of the compositions was sterile filtered using a sterile 0.22 micron Millex-GV PVDF filter syringe filter prior to administration.

For the study, naïve male Sprague Dawley rats were used that were between 10 to 12 months old. Blood samples were collected from the rats pre-dose and at the following time points after the dose: 5 min, 15 min, 30 min, 1 hr, 2 hr, 4 hr, 8 hr, 12 hr, and 18 hr. Five 0.5-ml to 1.0-ml blood samples were collected from each rat. Four of these samples were collected from the tail vein and the fifth sample was collected by cardiac puncture following deep anesthesia with isoflurane inhalation and exsanguination. In each study arm, rats were divided into two groups, group A and group B, that contained three rats each. Sample collection points were alternated between three rats in group A and three rats in group B. Thus, samples were collected from group A rats at pre-dose, 15 min, 1 hr, 4 hr and 12 hr. Samples were collected from group B rats at 5 min, 30 min, 2 hr, 8 hr and 18 hr. A thoracotomy was preformed to insure death. Each arm of the study used six rats for a total of 18 rats.

During the study following the subcutaneous and IV injections, the rats were observed for any clinical signs of adverse reactions. Behavior including licking, biting or scratching of the injection area, any loss of mobility, restlessness, unresponsiveness, and abnormal postures was monitored. No abnormal observations occurred, as the rats continued to act normally throughout the study.

Immediately after the rats were euthanized, the subcutaneous injection site along the back between the shoulders was examined for any signs of swelling or irritation. Three rats that received the 100 mg/ml Captisol® formulation for 12 hours and three rats that received the 300 mg/ml Captisol® formulation for 18 hours were compared to three naïve rats with no injection as a control. The epidermis of the rats was carefully removed, exposing the tissue directly surrounding the subcutaneous injection site. No swelling or signs of irritation were observed in the tissue.

Blood samples were stored in tubes containing EDTA as an anticoagulant and kept in an ice bath until centrifuged to separate the plasma. The plasma samples were stored at −20° C. until assayed. Plasma obtained from each of the samples was used for liquid chromatographic/mass spectroscopic analysis of the compound.

Plasma samples were analyzed for levosimendan and OR-1896 (the primary metabolite) by HPLC/MS/MS. A protein precipitation method was employed for sample preparation by the addition of an acetonitrile spiking solution or acetonitrile, and internal standard to a plasma sample or blank plasma. The internal standard for levosimendan was $^{13}C_6$-labeled levosimendan, and for OR-1896 was $^{13}C_6$-labeled ORM-25632 (racemic form of OR-1896). After addition of reagents, the mixture was vortexed and centrifuged. Approximately 75-80 µl was transferred to an autosampler vial with a plastic insert.

The HPLC/MS/MS method consisted of a Restek Raptor Biphenyl column, 2.7 µm, 100×3 mm. Mobile phase A consisted of 5 mM Ammonium Formate/0.1% Formic acid and mobile phase B was methanol. The flow rate was set to 0.6 ml/min and injection volume was 10 µl. Detection was performed with a Sciex 3200 Qtrap mass spectrometer in MRM mode.

Results

Figure 2:
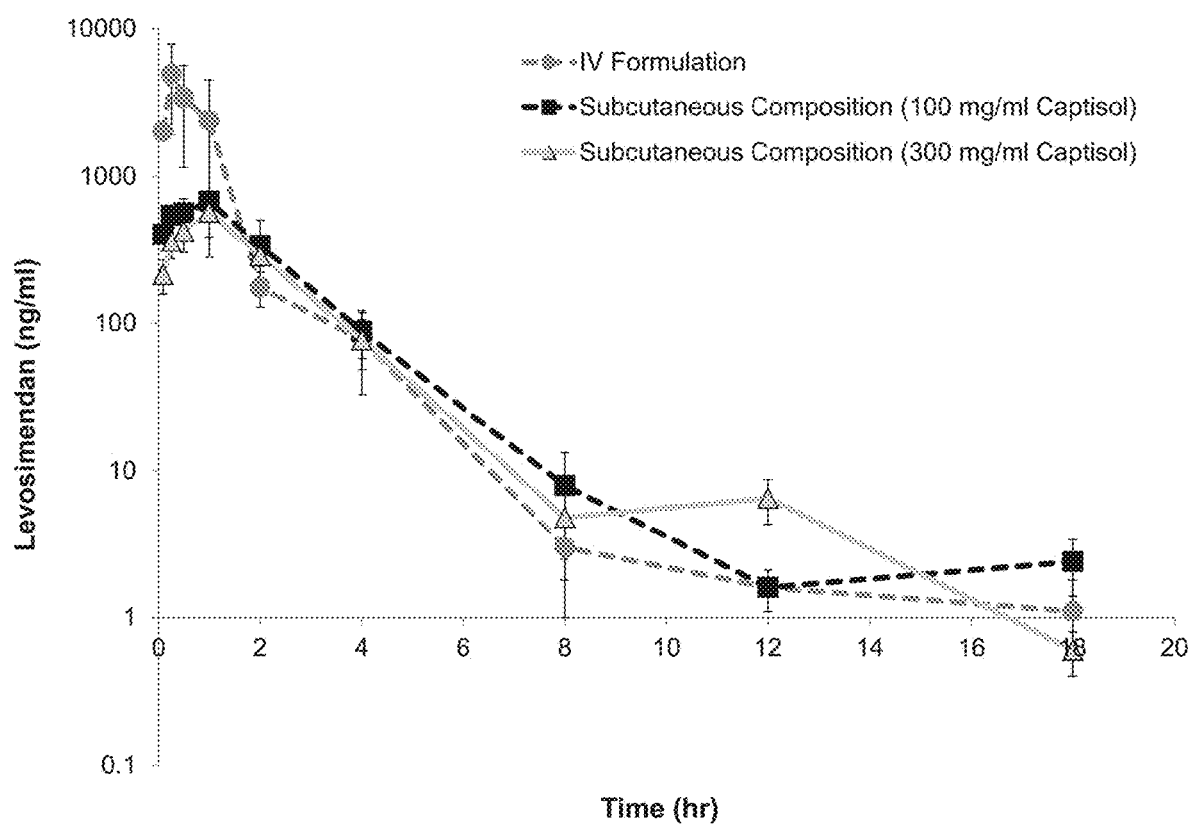
FIG. 2 shows mean levosimendan plasma concentrations after IV and subcutaneous dosing, as described in Example 3.

Plasma results for levosimendan are shown in Table 6 and in FIG. 2.

TABLE 6

Levosimendan plasma concentrations after IV and subcutaneous dosing.

| Time | IV Formulation | | Subcutaneous Composition (100 mg/ml Captisol ®) | | Subcutaneous Composition (300 mg/ml Captisol ®) | |
|---|---|---|---|---|---|---|
| | Concentration (ng/ml) | Std. Dev. | Concentration (ng/ml) | Std. Dev. | Concentration (ng/ml) | Std. Dev. |
| Pre-Dose | <LOQ | <LOQ | <LOQ | <LOQ | <LOQ | <LOQ |
| 5 min | 2013 | 180 | 402 | 19 | 213 | 56 |
| 15 min | 4890 | 2973 | 541 | 53 | 361 | 86 |
| 30 min | 3386 | 2238 | 564 | 139 | 422 | 119 |
| 1 hr | 2385 | 2105 | 673 | 83 | 568 | 183 |
| 2 hr | 175 | 46.5 | 337 | 166 | 287 | 42.8 |
| 4 hr | 77.2 | 44.5 | 87.7 | 30.3 | 77.0 | 28.6 |
| 8 hr | 3.0 | 2.0 | 7.9 | 5.4 | 4.8 | 3.0 |
| 12 hr | 1.6 | 0.5 | 1.6 | 0.2 | 6.5 | 2.2 |
| 18 hr | 1.1 | 0.7 | 2.4 | 1.0 | 0.6 | 0.2 |

LOQ = limit of quantitation

The higher initial plasma levels for the IV formulation are typical for an IV injection. The more rapid initial decrease in the blood levels (α phase) is the distribution of the drug throughout the tissues in the body. After the initial distribution of the drug, the loss of drug from the blood is mainly due to metabolism (β phase). In levosimendan, the β phase starts at about 2 hours. Notably, Table 7 and FIG. 2 show that the metabolism of levosimendan is very similar for the IV and the subcutaneous compositions. This is also supported by the nearly identical results for the plasma levels of the primary active metabolite, OR-1896.

Figure 3:
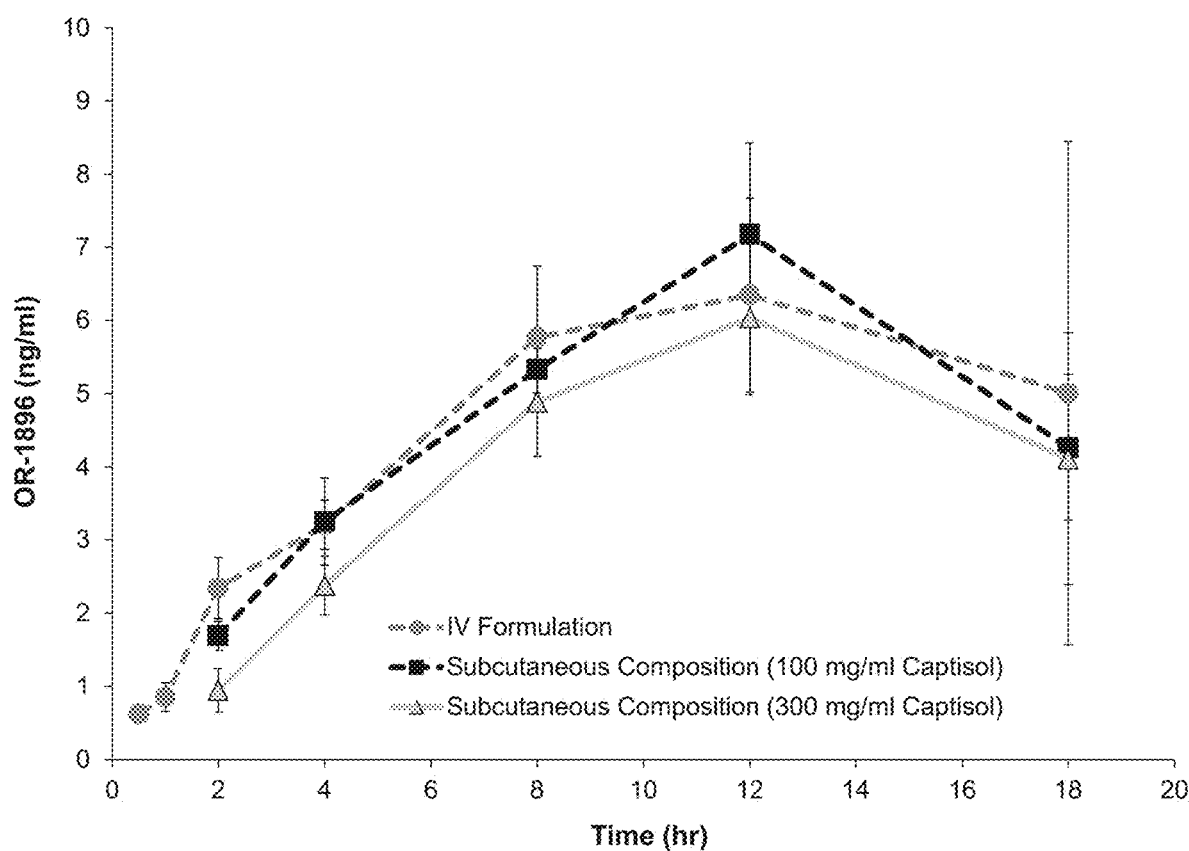
FIG. 3 shows mean OR-1896 plasma concentrations after IV and subcutaneous dosing, as described in Example 3.

Plasma results for OR-1896 are shown in Table 7 and in FIG. 3.

TABLE 7

OR-1896 plasma concentrations after IV and subcutaneous dosing.

| Time | IV Formulation | | Subcutaneous Composition (100 mg/ml Captisol ®) | | Subcuatenous Composition (300 mg/ml Captisol ®) | |
|---|---|---|---|---|---|---|
| | Concentration (ng/ml) | Std. Dev. | Concentration (ng/ml) | Std. Dev. | Concentration (ng/ml) | Std. Dev. |
| Pre-Dose | <LOQ | <LOQ | <LOQ | <LOQ | <LOQ | <LOQ |
| 5 min | <LOQ | <LOQ | <LOQ | <LOQ | <LOQ | <LOQ |
| 15 min | <LOQ | <LOQ | <LOQ | <LOQ | <LOQ | <LOQ |
| 30 min | 0.623 | 0.069 | <LOQ | <LOQ | <LOQ | <LOQ |
| 1 hr | 0.854 | 0.196 | <LOQ | <LOQ | <LOQ | <LOQ |
| 2 hr | 2.340 | 0.416 | 1.690 | 0.197 | 0.946 | 0.298 |
| 4 hr | 3.207 | 0.337 | 3.253 | 0.600 | 2.377 | 0.401 |
| 8 hr | 5.767 | 0.973 | 5.330 | 0.320 | 4.883 | 0.737 |
| 12 hr | 6.347 | 1.325 | 7.173 | 1.255 | 6.037 | 1.053 |
| 18 hr | 5.007 | 3.441 | 4.265 | 0.997 | 4.110 | 1.720 |

LOQ = limit of quantitation

OR-1896, the major active metabolite of levosimendan, demonstrated very similar plasma concentrations regardless of route of administration or formulation.

Pharmacokinetic parameters for both levosimendan and OR-1896 were calculated using a noncompartmental analysis by Phoenix WinNonlin (Cetera™ Version 6.3) software. Table 8 lists the pertinent pharmacokinetic values for levosimendan. A significantly lower $C_{max}$ was observed for both subcutaneous compositions versus the IV formulation, but the half-life for elimination was comparable for all formulations.

TABLE 8

Pharmacokinetic parameters for levosimendan after administration of the IV formulation and the subcutaneous compositions.

| Pharmacokinetic Parameter | Units | IV Formulation | Subcutaneous Composition (100 mg/ml Captisol ®) | Subcutaneous Composition (300 mg/ml Captisol ®) |
|---|---|---|---|---|
| $C_{max}$ | ng/ml | 4890 | 568 | 673 |
| $T_{max}$ | hr | 0.25 | 1 | 1 |
| $AUC_{(0-\infty)}$ | ng/ml*hr | 4932 | 1402 | 1699 |

TABLE 8-continued

Pharmacokinetic parameters for levosimendan after administration
of the IV formulation and the subcutaneous compositions.

| Pharmacokinetic Parameter | Units | IV Formulation | Subcutaneous Composition (100 mg/ml Captisol ®) | Subcutaneous Composition (300 mg/ml Captisol ®) |
|---|---|---|---|---|
| $K_{el}$ | $hr^{-1}$ | 0.942 | 0.683 | 0.632 |
| $T_{1/2}$ | hr | 0.736 | 1.015 | 1.097 |
| Cl | ml/hr/kg | 101 | n/a | n/a |
| F | % | n/a | 28 | 34 | n/a = not applicable;
$C_{max}$ = maximum plasma concentration;
$T_{max}$ = time to maximum plasma concentration;
AUC = area under the curve;
$K_{el}$ = elimination rate constant;
$T_{1/2}$ = elimination half-life;
Cl = clearance;
F = fluctuation The pharmacokinetic parameters for the active metabolite, OR-1896, are listed in Table 9. The $C_{max}$, $T_{max}$, and AUC for both subcutaneous compositions are very similar to the IV route of administration. The bioavailability of OR-1896 is 95-113% from the subcutaneous formulations.

TABLE 9

Pharmacokinetic parameters for OR-1896 after administration
of the IV formulation and the subcutaneous compositions.

| Pharmacokinetic Parameter | Units | IV Formulation | Subcutaneous Composition (100 mg/ml Captisol ®) | Subcutaneous Composition (300 mg/ml Captisol ®) |
|---|---|---|---|---|
| $C_{max}$ | ng/ml | 6.35 | 6.04 | 7.17 |
| $T_{max}$ | hr | 12 | 12 | 12 |
| $AUC_{(0-\infty)}$ | ng/ml*hr | 83.90 | 71.07 | 83.12 |
| F | % | n/a | 95 | 113 | n/a = not applicable;
$C_{max}$ = maximum plasma concentration;
$T_{max}$ = time to maximum plasma concentration;
AUC = area under the curve;
F = fluctuation These results show that OR-1896 plasma concentrations following administration of the subcutaneous compositions of the invention were comparable to those observed following IV levosimendan administration. This was an unexpected finding given the substantially lower $C_{max}$ and AUC of levosimendan observed following the subcutaneous administration of the compositions of the invention as compared to IV administration.

Figure 4:
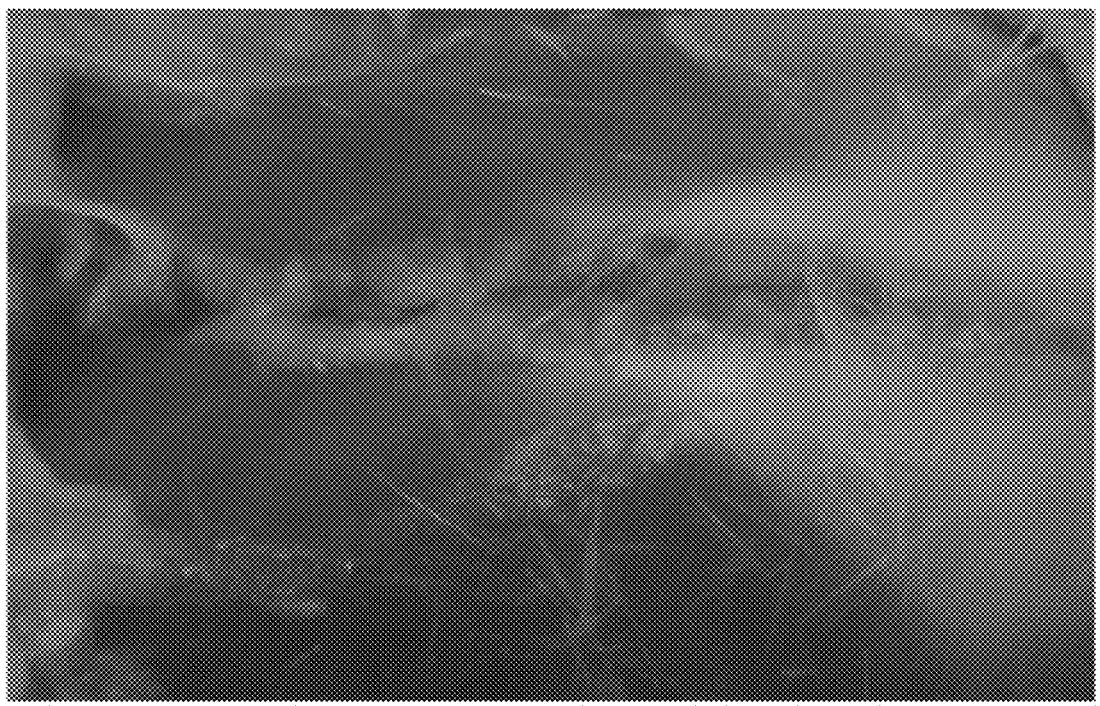
FIG. 4 is an image of the injection site of a rat with its epidermis removed, showing no visible signs of irritation, as described in Example 3.

In addition, there was no evidence of pain or visible signs of irritation at the injection site (see, e.g., FIG. 4), nor were there any clinical-related adverse events or other signs of pain or distress observed for the rats. The Captisol®-containing subcutaneous compositions did not cause any apparent irritation of adverse reactions when administered subcutaneously.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A method of treating a subject having a health condition, the method comprising subcutaneously administering to the subject in need thereof a pharmaceutical composition comprising
   (a) an effective amount of levosimendan;
   (b) a cyclodextrin derivative; and
   (c) one or more additional pharmaceutically acceptable additives,
   wherein the composition comprises a pH of about 5 to about 9.

2. The method of claim 1, wherein the cyclodextrin derivative comprises a beta-cyclodextrin derivative.

3. The method of claim 1, wherein the cyclodextrin derivative comprises a butyl ether spacer group, an alkyl ether space group, or a combination thereof.

4. The method of claim 1, wherein the cyclodextrin derivative comprises sulfobutylether.

5. The method of claim 1, wherein the cyclodextrin derivative comprises sulfobutylether beta-cyclodextrin.

6. The method of claim 1, wherein the cyclodextrin derivative is in an amount of about 50 mg/ml to about 400 mg/ml.

7. The method of claim 1, wherein the composition comprises a pH of about 6 to about 8.

8. The method of claim 1, wherein the one or more pharmaceutically acceptable additives comprise one or more non-citrate buffering agents.

9. The method of claim 1, wherein the one or more pharmaceutically acceptable additives comprise a phosphate buffer.

10. The method of claim 1, wherein the one or more pharmaceutically acceptable additives comprise one or more pH-modifying agents.

11. The method of claim 1, wherein the levosimendan is in an amount of about 0.1 mg/ml to about 100 mg/ml.

12. The method of claim 1, wherein the composition is substantially free of alcohol.

13. The method of claim 1, wherein the composition is preservative-free.

14. The method of claim 1, wherein the levosimendan is administered in an amount of about 0.1 mg/day to about 15 mg/day.

15. The method of claim 1, wherein the health condition is selected from the group consisting of heart failure, pulmonary hypertension, essential hypertension, secondary hypertension, chronic kidney disease, renal failure, nephropathy, chronic obstructive pulmonary disease, Raynaud's disease, peripheral vascular disease, cardio-renal syndrome, Alzheimer's, ALS, neurodegenerative disease, stroke, cerebrovascular disease, muscular dystrophy, congenital heart disease, and cardiomyopathy.

16. The method of claim 1, wherein the health condition is pulmonary hypertension due to heart failure with preserved ejection fraction.

17. The method of claim 1, wherein the method improves tolerance to administration of levosimendan relative to intravenous (IV) administration of levosimendan.

18. The method of claim 1, wherein the method delivers a levosimendan metabolite while minimizing peak plasma concentrations of levosimendan in the subject in need thereof.

19. The method of claim 1, wherein the administration is chronic.

* * * * *